United States Patent [19]

Russenberger

[11] 4,445,381

[45] May 1, 1984

[54] DEVICE FOR TESTING THE VIBRATION STRENGTH OF A TEST BODY

[75] Inventor: Max E. Russenberger, Bodman-Ludwigshafen, Fed. Rep. of Germany

[73] Assignee: Russenberger Prüfmaschinen AG, Schaffhausen, Switzerland

[21] Appl. No.: 230,897

[22] Filed: Feb. 2, 1981

[30] Foreign Application Priority Data

Feb. 11, 1980 [CH] Switzerland .......................... 1065/80

[51] Int. Cl.³ .............................................. G01N 29/04
[52] U.S. Cl. .......................................... 73/666; 73/668
[58] Field of Search .................. 73/666, 668, 663, 662

[56] References Cited

U.S. PATENT DOCUMENTS 3,090,226  5/1963  Corti et al. ............................ 73/666
3,123,728  3/1964  Kreiskorte ............................ 73/666

FOREIGN PATENT DOCUMENTS 716625  2/1980  U.S.S.R. ................................ 73/668

OTHER PUBLICATIONS

Rumul, 20 $M_p$ Testronic 7001 Brochure: Russenberger & Müller Scientific Instruments, Schaffhausen, Switzerland.

*Primary Examiner*—Anthony V. Ciarlante
*Attorney, Agent, or Firm*—Werner W. Kleeman

[57] ABSTRACT

A device for testing the fatigue vibration strength consists of a framework carrying a spring-mounted vibrating body, an electromagnetic exciter arranged between the vibrating body and one holding element to hold the test body. There is also an adjustable threaded spindle for the purpose of superimposing a static load on the vibrating load affecting a test body during a vibration strength test. The exciter is provided with two parts which are movable in relation to one another, the one part being connected to the vibrating body and the other to the aforementioned holding element. The two exciter parts are connected to one another by elastic rod shaped members. These are dimensioned in such a manner that in all foreseen operating conditions an air gap remains between the exciter parts permitting vibration excitation with good efficiency.

22 Claims, 5 Drawing Figures

DEVICE FOR TESTING THE VIBRATION STRENGTH OF A TEST BODY

FIELD AND BACKGROUND OF THE INVENTION

The present invention relates to a device for testing the vibration strength of a test body. The device comprises holding elements to removably hold the test body, with at least one of the holding elements being mounted in a way which allows it to vibrate. The device comprises an electromagnetic oscillation exciter with two parts that are movable in relation to one another for exciting vibrations. These two parts of the oscillation exciter are bridged by at least one elastic member. This elastic member is dimensioned in such a manner that it limits the displacements of the two oscillation exciter parts relative to one another. Therefore, in all foreseen operating conditions an air gap remains between the said two oscillation exciter parts permitting excitation with good efficiency.

A known device for a fatigue vibration strength test of test bodies, consists of a framework with elastic feet. The framework has a base standing on elastic feet. On the top side of the base there is a holding element, to hold the lower end of, for instance, a rod shaped, vertical test body. At the top of the framework there is a vertical threaded spindle which can be raised or lowered vertically. The lower end of the spindle is connected to a vibration body, which is also designated as the main moving mass, by means of a uncoupling pre-load spring, the former being provided with a holding element to hold the upper end of the test body. An electro-magnetic oscillation exciter has a first part with a magnet yoke, a magnetic core and a coil, which are also connected to the lower end of the threaded spindle; and a second part, i.e. an armature, which is movable in relation to the first part. The armature is relatively vertically adjustable with respect to the vibration body by manually operable adjustment means. There is also a transducer for the purpose of measuring the forces imparted to the test body. The transducer and the coil of the oscillation exciter are connected to the electronic circuits.

When testing the test body, it is made to vibrate, whereby the vibration body, which is connected to the upper end of the test body, also vibrates quite strongly. Moreover, the base connected to the lower end of the test body and the framework parts firmly connected to it, also vibrate a little. The pre-load uncoupling spring transmits only a small part of the vibration load from the vibration body to the threaded spindle, and therefore uncouples the vibrations of the vibration body from the threaded spindle. Hereafter, the totality of the mechanically vibrating parts will be called the oscillator. The excitation of vibrations is controlled by the electronic part in such a manner, that the oscillator vibrates at its natural vibration rate, so that during the test, adjustable vibrational or alternative forces are produced by the electronics. By adjusting the threaded spindle it is possible to superimpose via the pre-load uncoupling spring a static push or pull force on the alternating forces.

To allow the oscillation exciter to work, the air gap between the armature and the fixed part must be, on the one hand, wide enough to prevent the armature, when vibrating, to touch the fixed part of the oscillation exciter, and, on the other hand, it should not be so wide that the performance and efficiency of the exciter is adversely affected. However, the stroke of the vibrating armature depends on the required vibrating force and the rigidity of the test body. To allow the armature to vibrate freely, it is therefore sometimes necessary to widen the gap to such an extent that the efficiency is impaired. This of course is a considerable disadvantage. If one wants to always work with the different test bodies with the highest efficiency, it will be frequently necessary to alter the width of the gap by means of the already mentioned means of adjustment, a process that calls for additional work.

If on the occasion of a fatigue vibration strength test one adjusts a definite static push or pull force by means of the threaded spindle, the distance of the armature to the fixed part of the oscillation exciter also changes. When altering the static force, one is therefore often compelled to change the distance of the armature from the vibration body.

When carrying out a fatigue vibration strength test, the resonance of the oscillator is determined by the masses and elasticity of the various vibrating parts. Usually, the mass of the test body is small in comparison to the total mass of the oscillator, and the test body is also the part of the oscillator which is easiest to deform. If one imagines a oscillator, for simplicity's sake, built from a spring and a vibrating mass, the function of the spring is executed mainly by the test body, while the mass is about equal to the mass of the vibrating body. Correspondingly, the resonance frequency is also to a large extent determined by the spring-rate or -stiffness of the test body. For an oscillator consisting of a spring and a mass vibrating along a straight line, the resonance frequency is proportional to the square root of spring stiffness. The frequency therefore rises with the growing spring stiffness of the test body.

But it is also possible that other resonance vibrations with other vibration modes occur. In particular, the framework and other parts of the device generate natural frequencies, whose major parts are at least above a certain boundary frequency, which depends on the construction of the device and lies typically in the range of 300 Hz. One endeavours, therefore, as much as possible, to execute fatigue vibrating strength tests with a frequency below the above-mentioned boundary frequency. If the test is carried out with high frequencies, this may cause the test body to heat up due to the lost heat set free in it, a phenomenon that is generally undesirable. For this reason too one is inclined to keep the vibrating frequency low. But, as already mentioned, the resonance frequency of the oscillator depends to a large extent on the spring stiffness of the test body. For this reason one is often compelled to carry out tests with frequencies above the aforementioned boundary frequency, and this is also a serious disadvantage.

SUMMARY OF THE INVENTION

It is an object of the present invention to provide a device for testing vibration strength which makes it possible to avoid the disadvantages of the aforementioned device.

More particularly, it is an object of the present invention to provide a device for fatigue vibration tests, by which the dependence of the size of the vibration stroke of the vibrator's parts on the test body is reduced, so that for test bodies, whose stiffness covers a relatively large range, a favourable efficiency coefficient is obtained. Furthermore, it is no longer necessary to carry out adjustments to obtain a favourable air gap with each change of test bodies or with each change of superimposed static push or pull forces. Also, the present invention makes it possible to limit resonance frequencies of the oscillator to relatively small values for test bodies with considerable spring-stiffness.

In keeping with these objects and with others which will become apparent hereinafter, one feature of the present invention resides, briefly stated, in a device for testing the vibration strength of a test body, comprising a framework, holding elements to hold the test body, with at least one of the holding elements being able to vibrate, and at least one electromagnetic exciter having two vibration exciting parts that are movable in relation to one another, these parts being bridged by at least one elastic member.

The novel features of the present invention which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF PREFERRED EMBODIMENTS

Figure 1:
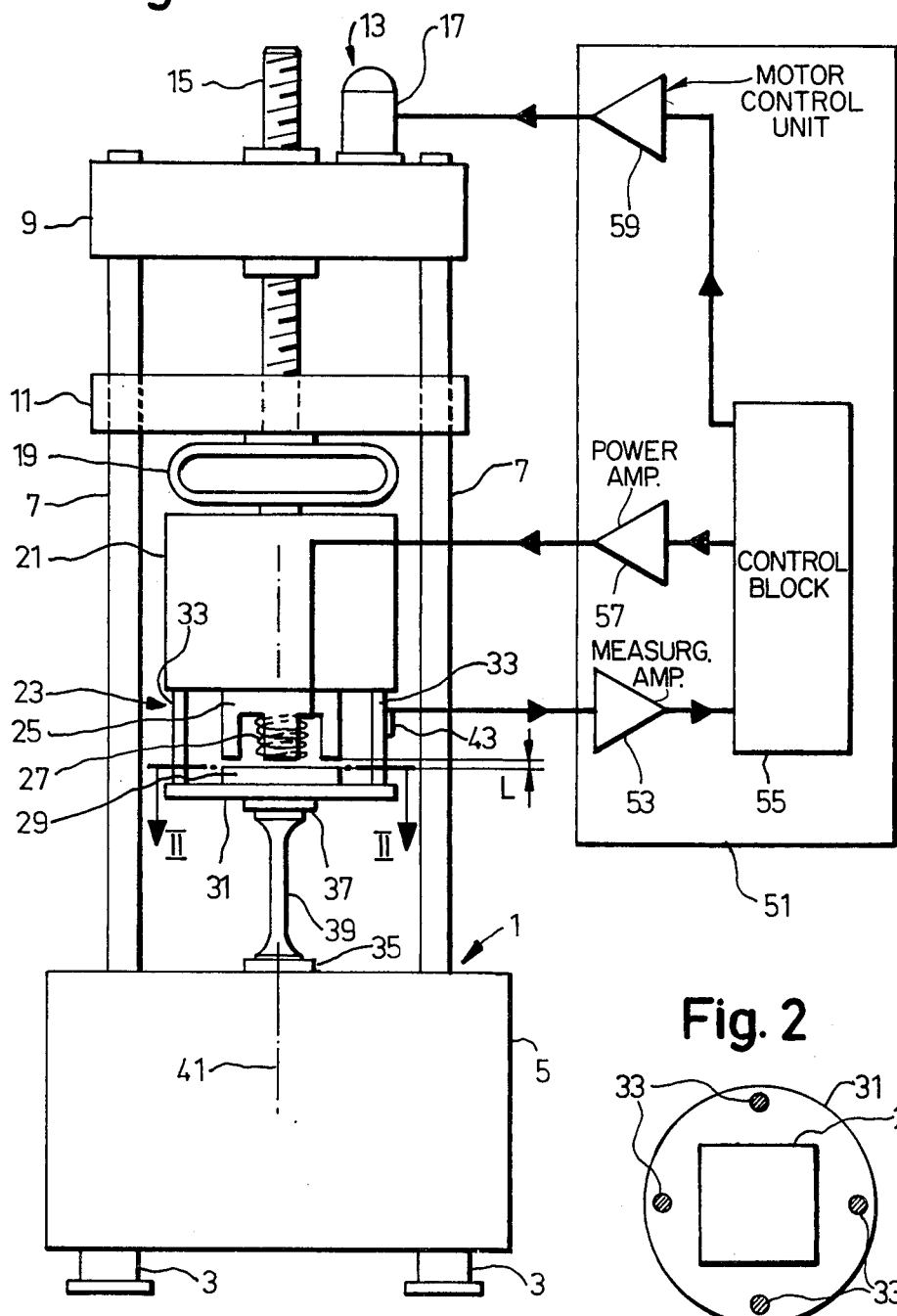
FIG. 1 is a diagrammatic view of a device for fatigue vibration strength tests with a block diagram of the electronic assembly.

The device for fatigue or endurance vibration strength tests of FIG. 1 shows the framework mark 1 as a whole. This is provided with elastic feet 3, bearing a base 5. The base 5 bears a yoke consisting of two rigidly assembled vertical columns 7 and a cross member 9. Between the base 5 and the cross member 9, a cross member forming a slide 11 is slidably vertically guided on columns 7. The slide 11 can be moved vertically by means of an adjusting device 13 having a threaded spindle 15 held in the cross member 9 and an electric motor 17. On the bottom side of slide 11, the upper leg of an uncoupling pre-load spring 19 is rigidly fastened (for clarity's sake the spring 19 has been swivelled 90°). The lower leg of spring 19 is rigidly fastened to a vibration body 21 which forms the main moving mass.

An electro-magnetic vibrator or oscillation exciter 23 is provided with a first part 25 made of ferromagnetic material, fastened to the lower side of the vibration body 21, the part 25 being provided with a magnetic core and a yoke with two legs, on whose core a coil 27 is fitted. The exciter 23 furthermore comprises a plate-shaped ferromagnetic second part 29, i.e. an armature movable in relation to the first part 25. The second exiter part 29 is rigidly connected to, for instance, a circular plate 31.

Figure 2:
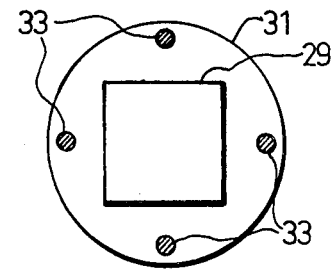
FIG. 2 is a section of the device along line II-II of FIG. 1.

The exciter 23 has four one-piece elastic members 33 in parallel, which also span and connect the exciter parts 25 and 29. Each one of the four elastic members 33 is formed, at least in its middle portion, by a cylindrical profile rod, whose lower end is rigidly fastened to the plate 31 and whose upper end is rigidly fastened to the vibrating body 21. As can be seen in FIG. 2, the four elastic members 33 are placed at equal distances on a circle around the exciter 23. The four elastic members 33 are made of non-ferromagnetic metal, e.g. of stainless steel. The base 5 and the plate 31 are each provided with a holding element 35 or 37. With these holding elements 35, 37, the test body 39, formed by a vertical rod, is removably held. The base 5, the threaded spindle 15, the spring 19, the vibration body 21, the exciter 23 and other parts are arranged in an essentially symmetrical pattern around the vertical axis 41. The device moreover has at least one force measuring transducer 43 for the purpose of measuring the forces exerted on the test body 39. This transducer may be formed by at least one resistance strain gauge mounted on at least one of the elastic members 33.

The device furthermore has an electronic assembly 51. This is provided with a measuring amplifier 53, whose input end is connected to the transducer 43 and its output with a control block 55. The control block 55 is connected with the input side of a power amplifier 57 whose output is connected to coil 27 of the exciter 23. The control block 55 is moreover connected to the motor control unit 59, which is connected to motor 17. The control block can be set by manually operable control elements to adjust various values and parameters, such as the amplitude of the vibrator force and the static push or pull force. The control block 55 has further means for varying certain values during tests according to a chosen programme.

If the test body 39 is to be subjected to a fatigue vibration strength test, vibrations are generated by the exciters parallel to the axis 41. Thereby the test body 39 and other parts are caused to vibrate, particularly the vibration body 21 and the elastic members 33. The vibration body 21 will then be uncoupled from the remaining framework by the spring 19. Moreover the base 5 and the yoke connected with it will follow the vibrations a little, but the vibration amplitude of the base and of the yoke will then be relatively small, because these parts have a large mass. The base 5 is also termed the opposing mass, in comparison to the vibration body 21 that forms the so-called main moving mass. The mechanically vibrating elements of the device, taken as a whole, form an oscillator. The electronic assembly part 51 forms a feed-back circuit and is built in such a manner that the oscillator is excited by its resonance frequency.

The elastic members 33, formed by rods, when they are vibrating act as longitudinal springs, i.e. they are elastically deformed in a vertical direction. The spring rate or spring stiffness of the elastic members 33 in that case depends upon the surface of the section and the module of elasticity of the material used for the members 33.

The elastic members 33 are made in such a manner that in all operating conditions a free air gap exists between the movable part 29 and the fixed part 25 of the exciter 23. Measured along axis 41, the instantaneous dimension of the gap shall have the value L. The elastic members 33 are moreover formed in such a manner that the excitation within the whole operating range of the device will have a high degree of efficiency. The design of the elastic members 33 will now be discussed further.

To begin with, the length of the elastic members 33 is such, that with an unloaded test body, or if no test body is present, an air gap exists between vibrator parts 25 and 29.

The device can, for instance, be arranged for a maximum vibrator load to be exerted on the test body as specified by a data sheet, of ±125 kN, and for a maximum stroke of the vibration body 21 relative to the base 5 of ±1.5 mm. By adjustment of the slider 11 parallel to axis 41, it is possible to superimpose on the vibrating force attacking the test body during vibration via the uncoupling pre-load spring yet another static, i.e. a constant-in-time push or pull force. For each device it is usual to prescribe a maximum static force or load, specified by a data sheet, that may be exerted on the test body. The device may, for instance, be conceived for a maximum static load of ±125 kN. When performing a fatigue vibration strength test, the elastic members 33 are hence submitted to an alternating load and, possibly, in addition, to a superimposed static load. The spring stiffness of the elastic members 33 is now tuned to their length in such a manner that the elastic members 33, even under maximum static push or pull loads and under the simultaneous impact of the maximum foreseen vibrating loads, are deformed only elastically. The spring stiffness of the elastic members 33 is chosen so that under maximum static compression load and also under maximum compression by vibration, an air gap remains between the exciter parts 25 and 29.

The spring stiffness of the elastic members 33 is such, for instance, that the length of the elastic members 33, and therefore also dimension L of the air gap, starting with the unloaded state at the admission of a test body with the foreseen static maximum load, varies at most by ±1 mm, preferably at most by ±0,5 mm and for instance by a maximum of ±0.3 mm. The spring stiffness is such that the air gap dimension L, due to the maximum vabration load, varies at most only by ±1 mm, preferably at most by ±0.5 mm and for instance at most by ±0.3 mm. The air gap dimension L can then amount to e.g. 0.6 to 1 mm with resting, unloaded elastic members 33.

For the rest, the total spring stiffness of the parallel elastic members 33 is at least five times, preferably at least ten times, and perhaps ten to twenty times higher than the spring stiffness of the uncoupling pre-load spring 19.

The elastic members 33 bridging the exciter 23 transmit together at least 90% and, preferably, at least or about 99% of the vibration load exerted on the test body 39. The uncoupling pre-load spring, on the other hand, transmits at most 20% and preferably, at most 10% of the vibration load applied from vibration body 21 to the threaded spindle 15.

The transmission of forces between the vibration body 21 and the test body 39 is, thus mainly enacted via the elastic members 33, whilst the exciter 23 transmits only a comparatively small part of the forces. This means that the vibration force imparted to the test body 39 is at least 100 times larger because of the resonant elevation, and possibly a hundred to a thousand times larger, for the same reason, than the force generated by the exciter 23.

To avoid too much deformation of the elastic members 33 by the static load and by the alternating vibration forces, the spring stiffness of the elastic members 33 must have a certain minimum value as follows from the previous discussion. But this spring stiffness of the elastic members 33 must not be exaggerated. Regarding the design of the exciter 23, it would be expedient that the stroke of the exciter part 25 not become too small, since the exciter, in the case of a fatigue vibration strength test, must supply the energy which is used up by the vibrating elements, owing to damping. In a deivce designed for a maximum vibration load of 125 kN, it is possible that maximum power is needed to compensate damping losses which for instance, may be close to 500 W. The spring stiffness of the elastic members 33 should preferably be so dimensioned that the stroke of part 29 in relation to part 25, starting from rest position, be at least ±0.1 mm and, for instance, at least or about ±0.3 mm, if the exciter 23 receives maximum electric power.

As already mentioned, the oscillator formed by the entirety of the mechanically vibrating elements of the device, vibrates with its resonance frequency or, more precisely, with its fundamental resonant frequency for up-and-down oscillations. The resonant frequency of the oscillator is determined by the masses of the various oscillator parts and their elasticity. But the oscillator behaves similarly to a spring with a vibrating mass, held by the spring and moving up and down parallel to axis 41, whereby the spring is approximately represented by the test body 39 and the vibrating mass approximately by the masses of vibration body 21 and exciter 23, the main moving mass being formed by the vibration body 21.

Figure 3:
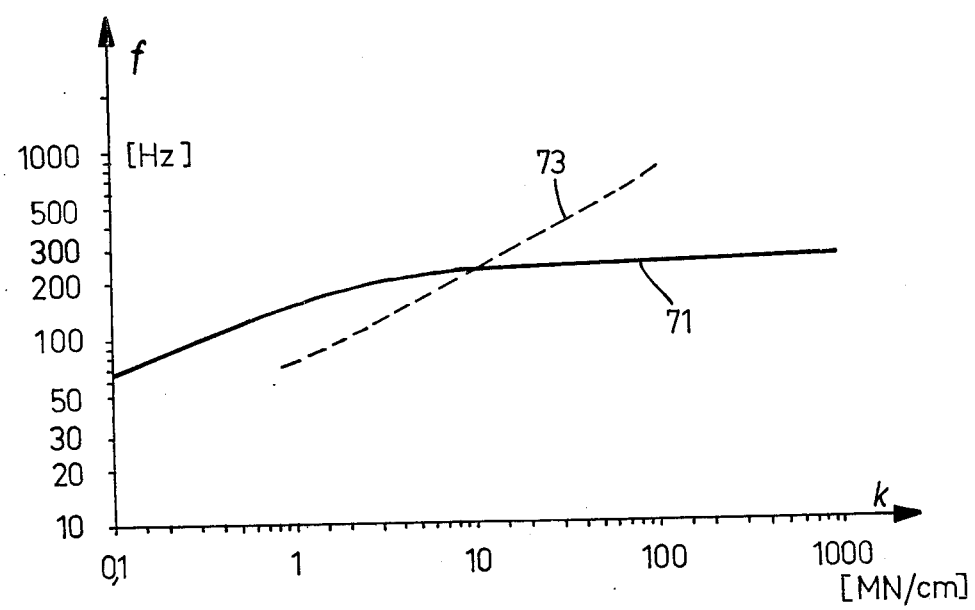
FIG. 3 is a diagram showing the dependence of resonance frequencies on spring stiffness of the test body.

The device as designed for a maximal vibrating load of ±125 kN, for the purpose of providing an example, according to the invention, for a fatigue vibration strength test, shows a dependence of the resonance frequency f of the fundamental oscillation of the spring rate of spring stiffness k of the test body as represented in FIG. 3 by the curve 71. Within the range of spring stiffness k, extending from about 0.1 to 1 MN/cm, the resonant frequency rises quite steeply with increasing spring stiffness from about 65 to 150 Hz. Thereafter the gradiant diminishes with increasing spring stiffness k, so that the resonance frequency at 1000 MN/cm reaches about 260 Hz.

For comparison, yet another curve 73 is drawn in FIG. 3, which shows the relationship between spring stiffness and resonance frequency for a device unlike the instant inventive device without elastic members 33. Curve 73 rises rather steeply in the spring stiffness range under review, extending approximately from 1 to 100 MN/cm, from about 75 to about 700 Hz, forming, in the double-logarithmic representation, almost a straight line, crossing curve 71 at a stiffness of about 10 MN/cm.

In the device built according to the invention, equipped with elastic members 33, the resonant frequency therefore rises only to about the quadruple of the initial value over a spring stiffness range of four decades, whereas the resonant frequency in a device without elastic members 33 reaches more than the ninefold initial value over a spring stiffness range of only two decades. The elastic members 33 therefore ensure that the resonant frequency for which the device is designed, never exceeds the boundary value of 300 Hz. The device is conceived in such a manner, that the most important natural resonances of the framework, or at least the majority of them, lie above the above-mentioned boundary frequency.

Figure 4:
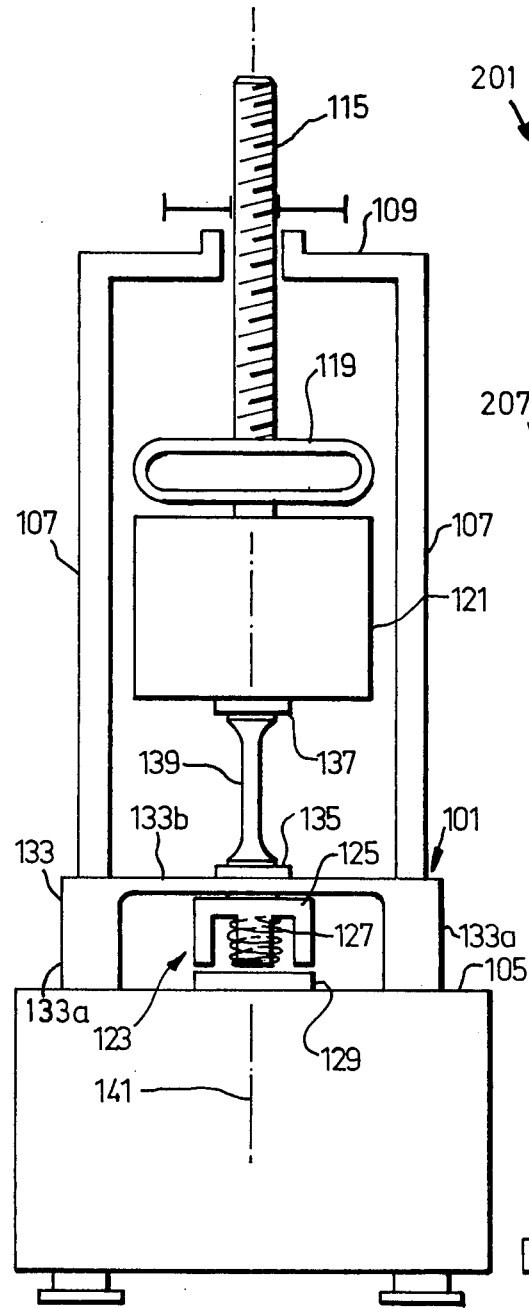
FIG. 4 is a diagrammatic view of an alternate embodiment of a device for a fatigue vibrating strength test.

The embodiment of the device shown in the very simplified key plan FIG. 4 shows an framework 101 with a base 105 as a opposing mass. A one-piece, yoke-shaped elastic member 133 of non-ferromagnetic metal is provided with two massive and essentially rigid posts 133a, whose lower ends are fastened to base 105. The upper ends of the posts 133a are bridged by a flat, horizontal web, forming a flexible spring 133b. The columns 107 are mounted on the posts 133a. At their top, the columns 107 are joined by a cross member 109. An adjustable threaded spindle 115, held in the cross member 109, is connected at its lower free end to a vibration body 121 via a spring 119. An exciter 123 is placed between the base 105 and the flexing spring 133b. The exciter 123 is provided with a yoke and a core forming an first part 125 and carrying a coil 127, the first part 125 being rigidly connected with the middle portion of the elastic member 133b. A plate shaped second part 129 is connected to the base 105. The flexing spring 133b has a holding element 135 on the upper side of its middle portion. Another holding element 137 is mounted to the bottom of the vibration body 121.

There is also at least one not shown force-measuring transducer, which may be situated between the elastic member 133b and the holding element 135. There are also: a device for the setting of the threaded spindle 115 and an electronic assembly.

When carrying out a fatigue vibration force test, the holding elements 135, 137 hold a test body 139 and vibrate relative to one another and parallel to the vertical axis 141. The two exciter parts 125, 129 move up and down relative to one another in operation and are thus joined via the elastic member 133 with its flexing spring 133b. At rest, the flexing spring 133b is at a right angle (90°) and its middle portion, when vibrating, moves up and down parallel to axis 141. For the rest, the elastic member 133 is designed according to the analogous criteria used for the elastic members 33.

The embodiment shown in FIG. 5, again a simplified key plan, shows a framework 201 which, instead of the blocks 5, 105, has only a comparatively light lower part 205, carried on sprung feet, on which a yoke with two columns 207 and a cross member 209 is built. The cross member has a vertically adjustable threaded spindle 215, whose lower end is connected via a spring 219 with a vibration body 221. A plate 231 is connected by rod shaped elastic members 233 to the vibration body 221. Between this latter and plate 231, there is an electromagnetic vibrator 223 connected with a vibration body 221 carrying a part 225 with a coil 227, and a part 229 mounted on plate 231. The lower part 205 is connected with a vibration body 263 via a spring 261. On this vibration body 263, a ferromagnetic part 275, carrying a coil 277 of an electromagnetic exciter 273, is fastened, whose other ferromagnetic part 279 is connected to a plate 281. This plate is connected by elastic rod shaped members 283 to the vibration body 263. The plates 281 and 231 have each a holding element 235 or respectively 237. These two holding elements 235, 237 hold a test body 239, which during a vibration strength test, will be stretched and compressed parallel to axis 241.

The two vibration bodies 221 and 263 have an equal mass and the exciters 223 and 273 are identical and symmetrically mounted. The parallel elastic members 233 and 283 are also identical. In addition, the elastic members 233, 283 are dimensioned according to the same criteria as those for the elastic members 33.

It is to be noted that the elastic member 133 shown in FIG. 4, instead of being yoke shaped, could be made rotation-symmetrical to the axis 141. The elastic member then would have the shape of a dome open below, and the flexling spring would be a circular membrane held along its whole circumference.

Figure 5:
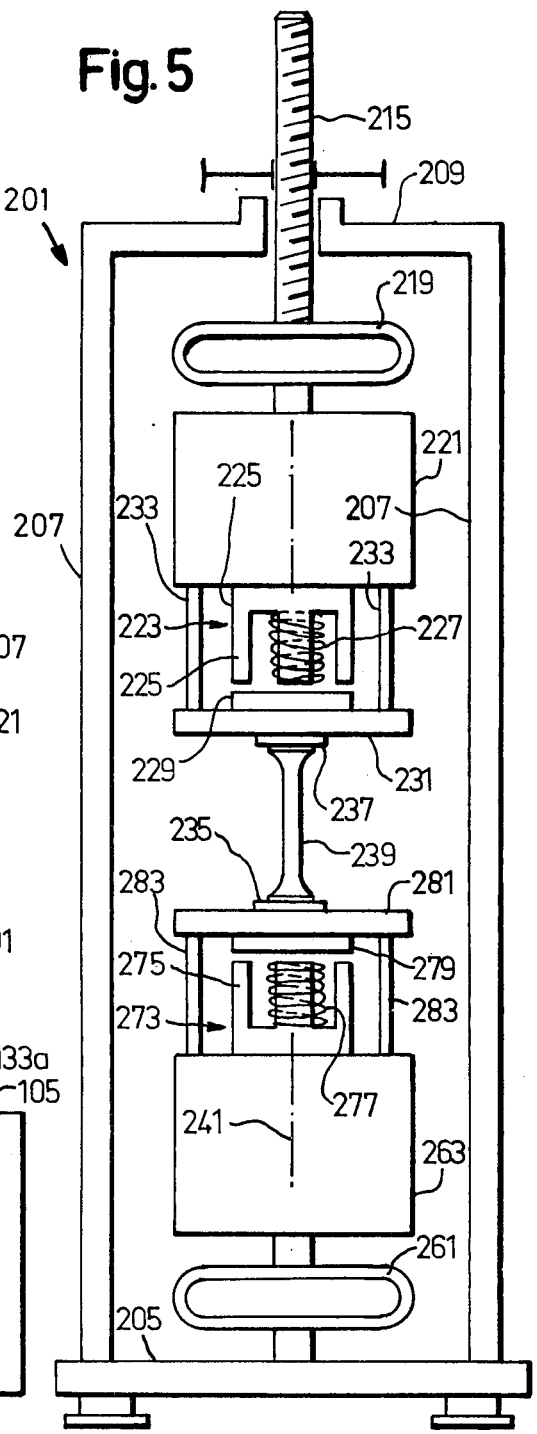
FIG. 5 is a diagrammatic view of another embodiment of the device.

It would also be possible to replace the rod-shaped elastic members shown in FIG. 5 by elastic members with flexing springs.

Of course the test bodies may not only be tested for their axial elongation- and compression-strength, but also, with a corresponding modification of the holding elements, for their bending- and torque-strength.

While specific embodiments of the invention have been shown and described in detail to illustrate the application of the principles of the invention, it will be understood that the invention may be embodied otherwise without departing from such principles.

What is claimed is:

1. A device for testing the vibration strength of a test body, comprising:
   a framework;
   holding elements to hold the test body on opposite sides thereof,
   at least one vibration body operatively connected with one of said holding elements;
   at least one uncoupling spring for decoupling said at least one vibration body and said one holding element connected therewith from the framework so that said at least one vibration body and said one holding element are able to vibrate;
   at least one electromagnetic exciter having two parts that are movable in relation to one another for vibration excitation;
   at least one elastic member;
   supply means for supplying electrical energy to said at least one electromagnetic exciter, so that an oscillator comprising said at least one vibration body, said test body, and said at least one elastic member can be excited by said at least one electromagnetic exciter at its resonance frequency;
   one portion of said elastic member being connected to one of said holding elements in such a substantially direct manner that said at least one vibration body has a mass greater than the total mass of said test body, said at least one elastic member and movable members arranged between said at least one elastic member and the test body to be held; and
   said two parts of said at least one electromagnetic exciter are bridged by said at least one elastic member.

2. A device, according to claim 1, wherein elastic members are arranged around said exciter, these elastic members being connected at one end each to one each of said exciter parts, whose longitudinal axes are parallel to the axis along which the said exciter parts are moving, relatively to one another when exciting vibrations.

3. A device, according to claim 2, wherein at least the middle portion of the elastic member is a profiled rod.

4. A device, according to claim 1, wherein said elastic member comprises a flexible spring forming an angle with the axis, parallel to which, when vibrations are excited, the said exciter parts are moving.

5. A device, according to claim 4, wherein the flexible spring is connected in its middle with one part of said exciter and on opposite sides with the other part of the exciter.

6. A device, according to claim 1, wherein one of the two exciter parts, which are movable in relation to one another, and a portion of the elastic member, are connected with said vibration body to vibrate, attached to the framework, and wherein the other exciter part and another portion of the elastic member are connected to a holding element.

7. A device, according to claim 1, wherein the elastic member is formed in such a manner that the exciter parts, that are movable in relation to one another, may only move away from their rest position by at most ±1 mm due to maximum vibration excitation.

8. A device, according to claim 1, wherein there is further provided adjustable means for superimposing a static load to the vibrating load affecting the test body, and wherein the elastic member is formed in such a manner that the said exciter parts cannot be moved by the maximum static load for more than ±1 mm from their rest position.

9. A device, according to claim 1, wherein the elastic member or elastic members are formed in such a manner than the elastic member or the parallel elastic members transmit at least 90% of the force exerted on the test body when being submitted to a vibration strength test.

10. The device according to claim 1, further including:
    an adjusting device for adjusting and imposing a substantially static pushing or pulling force on the test body;
    said adjusting device comprising means displaceable parallel to a predetermined direction along which said exciter parts are movable in relation to one another relative to the framework; and
    one end of said at least one uncoupling spring being connected to said at least one vibration body and the other end thereof being connected to said displaceable means.

11. The device according to claim 1, further including:
    at least one transducer for sensing the vibrations and electrically connected to said supply means to that the transducer, the supply means and the exciter form a feed-back circuit for exciting the oscillator at its resonance frequency; and
    said transducer comprising a strain gauge mounted to said at least one elastic member.

12. The device according to claim 1, wherein:
    the spring stiffness of said at least one elastic member is higher than the spring stiffness of said at least one uncoupling spring.

13. The device according to claim 1, wherein:
    said at least one elastic member comprises a plurality of substantially parallel elastic members; and
    the total spring stiffness of said plurality of elastic members is higher than the spring stiffness of said at least one uncoupling spring.

14. The device according to claim 1, wherein:
    the spring stiffness of said at least one elastic member is at least five times higher than the spring stiffness of said at least one uncoupling spring.

15. The device according to claim 1, wherein:
    said at least one elastic member comprises a plurality of substantially parallel elastic members; and
    the total spring stiffness of said plurality of elastic members is at least five times higher than the spring stiffness of said at least one uncoupling spring.

16. A device for testing the vibration strength of a test body, comprising:
    a framework;
    holding elements to hold the test body on opposite sides thereof;
    at least one uncoupling spring;
    at least one vibration body;
    at least one electromagnetic exciter having two parts that are movable in relation to one another for vibration excitation;
    at least one elastic member;
    supply means for supplying electrical energy to said at least one electromagnetic exciter, so that an oscillator comprising said at least one vibration body, said at least one elastic member and the test body can be excited by said electromagnetic exciter at its resonance frequency;
    one end of said at least one uncoupling spring being connected to the framework and the other end thereof to said at least one vibration body so that the latter is able to vibrate relative to the framework;
    said at least one elastic member being disposed between said at least one vibration body and one of said holding elements; and
    said two parts of said at least one electromagnetic exciter being bridged by said at least one elastic member.

17. The device according to claim 16, wherein:
    said at least one elastic member being disposed between said one holding element and said at least one vibration body; and
    a further one of said holding elements being attached to the framework.

18. The device according to claim 16, wherein:
    two said vibration bodies, at least two said elastic members and two said uncoupling springs are provided;
    each of said two vibration bodies being connected by one of said uncoupling springs to the framework and by a respective one of said at least two elastic members to a respective one of said holding elements, so that during a test there are disposed between each of the two opposite sides of the test body and the framework an uncoupling spring, a vibration body, and at least one of said elastic members.

19. A device, according to claim 18, wherein there are provided two electromagnetic exciters connected with different holding elements, which are provided each with two exciter parts which are movable in relation to one another, for purpose of exciting vibrations, and wherein each exciter is bridged with at least one elastic member, which interconnects the parts of the relative exciter which are movable in relation to one another.

20. The device according to claim 16, further including:
    an adjusting device for adjusting and imposing a substantially static pushing or pulling force on the test body;
    said adjusting device comprising means displaceable parallel to a predetermined direction along which said exciter parts are movable in relation to one another relative to the framework; and
    one end of said at least one uncoupling spring being connected to said at least one vibration body and the other end thereof being connected to said displaceable means.

21. The device according to claim 16, further including:

at least one transducer for sensing the vibrations and electrically connected to said supply means so that the transducer, the supply means and the exciter form a feed-back circuit for exciting the oscillator at its resonance frequency; and said transducer comprising a strain gauge mounted to said at least one elastic member.

22. A device for testing the vibration strength of a test body, comprising:

a framework;

holding elements to hold the test body on opposite sides thereof;

an uncoupling spring;

a vibration body;

an electromagnetic exciter having two parts that are movable in relation to one another for vibration excitation;

at least one elastic member bridging said two electromagnetic exciter parts;

supply means for supplying electrical energy to said at least one electromagnetic exciter, so that an oscillator comprising said vibration body, said at least one elastic member and the test body can be excited by said electromagnetic exciter at its resonance frequency;

one end of said uncoupling spring being connected to the framework and the other end thereof to said vibration body so that the latter is able to vibrate relative to the framework; and one of said two exciter parts and a portion of said at least one elastic member being attached to the framework and the other of said two exciter parts and another portion of said at least one elastic member being connected to one of said holding elements and another of said holding elements being attached to said vibration body.

* * * * *